United States Patent [19]
Schmid et al.

[11] Patent Number: 5,624,486
[45] Date of Patent: *Apr. 29, 1997

[54] MULTIPLY COATED METALLIC LUSTER PIGMENTS

[75] Inventors: Raimund Schmid, Neustadt; Norbert Mronga, Dossenheim, both of Germany

[73] Assignee: BASF Aktiengesellschaft, Ludwigshafen, Germany

[*] Notice: The term of this patent shall not extend beyond the expiration date of Pat. No. 5,626,661.

[21] Appl. No.: 297,857

[22] Filed: Aug. 30, 1994

[30] Foreign Application Priority Data

Feb. 21, 1994 [DE] Germany ............ 44 05 492.0

[51] Int. Cl.$^6$ ............................................. C09C 1/62
[52] U.S. Cl. .............. 106/404; 106/31.65; 106/415; 106/417; 106/439; 106/459; 106/472; 106/474; 106/479; 427/213; 427/216; 427/217; 427/218; 427/250; 427/255.1; 427/255.2
[58] Field of Search ................... 106/415, 417, 106/439, 459, 472, 474, 479, 404, 23 C; 427/213, 216, 217, 218, 250, 255.1, 255.2

[56] References Cited

U.S. PATENT DOCUMENTS

| | | | |
|---|---|---|---|
| 2,885,366 | 5/1959 | Iler | 252/313.2 |
| 3,053,683 | 9/1962 | Yolles | 106/403 |
| 3,074,801 | 1/1963 | Gessler et al. | 106/403 |
| 3,438,796 | 4/1969 | Hanke | 106/403 |
| 3,767,443 | 10/1973 | Clark et al. | 106/415 |
| 4,328,042 | 5/1982 | Ostertag et al. | 106/403 |
| 4,552,593 | 11/1985 | Ostertag | 106/418 |
| 4,676,838 | 6/1987 | Franz et al. | 106/418 |
| 4,867,793 | 9/1989 | Franz et al. | 106/415 |
| 4,879,140 | 11/1989 | Gray et al. | 427/490 |
| 4,978,394 | 12/1990 | Ostertag et al. | 106/404 |
| 5,026,429 | 6/1991 | Mronga et al. | 427/213 |
| 5,059,245 | 10/1991 | Phillips et el. | 106/22 C |
| 5,277,711 | 1/1994 | Schmidt et al. | 106/404 |
| 5,364,467 | 11/1994 | Schmid et al. | 106/403 |

FOREIGN PATENT DOCUMENTS

| | | |
|---|---|---|
| 0313281 | 4/1989 | European Pat. Off. . |
| 0353544 | 2/1990 | European Pat. Off. . |
| 0571836 | 12/1993 | European Pat. Off. . |
| 43 19 669 | 1/1994 | Germany . |
| 42 23 384 | 1/1994 | Germany . |
| 42 36 332 | 5/1994 | Germany . |
| 42 41 753 | 6/1994 | Germany . |

OTHER PUBLICATIONS

Derwent abstract 90–037778/06 of DE 3825702–A, Hild et al., "Novel goniochromatic pigment —used in security and effect inks", Feb. 1990.

Derwent abstract 94–17373 of DE 43 19 669, Schmidt et al. Jan. 13, 1994.

Farbe & Lack–97, Forschung & Entwicklung, Robert Besold, et al., "Aluminiumpigmente Fur Wasserige Beschichtungen–Widerspruch Oder Wirklichkeit", Apr. 1991, pp. 311–314.

*Primary Examiner*—Mark L. Bell
*Assistant Examiner*—Scott L. Hertzog
*Attorney, Agent, or Firm*—Oblon, Spivak, McClelland, Maier & Neustadt, P.C.

[57] ABSTRACT

Luster pigments based on multiply coated plateletlike metallic substrates comprising A) a first layer consisting essentially of silicon oxide, aluminum oxide and/or aluminum oxide hydrate, B) a second layer consisting essentially of metal and/or nonselectively absorbing metal oxide, and C) if desired, a third layer consisting essentially of colorless or selectively absorbing metal oxide.

10 Claims, No Drawings

MULTIPLY COATED METALLIC LUSTER PIGMENTS

The present invention relates to novel luster pigments based on multiply coated platelet-shaped metallic substrates comprising A) a first layer consisting essentially of silicon oxide, silicon oxide hydrate, aluminum oxide and/or aluminum oxide hydrate, B) a second layer consisting essentially of metal and/or nonselectively absorbing metal oxide, and C) if desired, a third layer consisting essentially of colorless or selectively absorbing metal oxide, obtainable by a) wet-chemical coating of the substrate particles with silicon oxide, silicon oxide hydrate, aluminum oxide and/or aluminum oxide hydrate by hydrolytic decomposition of organic silicon and/or aluminum compounds in which the organic radicals are attached to the metals via oxygen atoms in the presence of an organic solvent in which the metal compounds are soluble with or without subsequent drying, b) further coating of the particles obtained in step a) with metal by b1) gas phase decomposition of volatile metal compounds in an inert atmosphere or b2) electroless, wet-chemical metal deposition with or without subsequent drying or with nonselectively absorbing metal oxide by b3) gas phase decomposition of volatile metal compounds in the presence of oxygen and/or water vapor and c) if desired additional coating of the particles obtained in step b) with colorless or selectively absorbing metal oxide by c1) gas phase decomposition of volatile metal compounds in the presence of oxygen and/or water vapor or c2) wet-chemical coating by hydrolytic decomposition of organic metal compounds in which the organic radicals are attached to the metals via oxygen atoms in the presence of an organic solvent in which the metal compounds are soluble and subsequent drying.

The invention also relates to mixtures of these pigments (I) with multiply coated silicatic platelets (II) comprising A') a first layer consisting essentially of colorless or selectively absorbing metal oxide, B') a second layer consisting essentially of metal and/or nonselectively absorbing metal oxide, and C') if desired, a third layer consisting essentially of colorless or selectively absorbing metal oxide, as essential components, The invention further relates to the production of these pigments and pigment mixtures and their use for coloring coatings, inks, including printing inks, plastics, glasses and ceramic products.

Luster effect pigments are used in many sectors of industry, for example in automotive coatings, decorative coatings, plastics pigmentation, paints, printing inks, especially security printing inks, and cosmetics.

Their optical effect is based on the directed reflection of light at predominantly sheetlike, mutually parallel-oriented, metallic or strongly refractive pigment particles. Depending on the composition of the pigment platelets, interference, reflection and absorption phenomena create angle-dependent color and lightness effects.

Owing to their uncopyable optical effects, these pigments are increasingly gaining in importance for the production of forgery-proof security documents, such as banknotes, checks, check cards, credit cards, tax stamps, postage stamps, rail and air tickets, telephone cards, lottery tickets, gift vouchers, passes and identity cards.

Markings prepared with the luster effect pigments and the absence of these markings or their alteration, for example in a color copy (disappearance of color flops and luster effects), are safely discernible by the unaided, naked eye and so make it easy to distinguish the original from the copy.

U.S. Pat. No. 3,438,796, U.S. Pat. No. 4,879,140 and U.S. Pat. No. 5,059,245 disclose special effect pigments with alternating metal and metal oxide layers, but these pigments differ from the pigments of the invention in their manner of production.

The pigments described there are produced by physical techniques such as vacuum deposition onto a substrate which may be provided with a soluble coating or is itself soluble, separation from the substrate, and subsequent comminution, or by plasma decomposition, subsequent deflaking of the decomposition product from the reactor walls, and blowing out.

In the pigments obtained in this way, the substrate function is performed by a central layer which, unlike the substrate particles of the invention, is not completely enclosed by the other layers. The layered structure is visible at the faces formed by the process of comminution, nor is there any outer confining layer and this can also lead to instabilities, for example in aqueous systems.

Also, these production processes are very costly and time-consuming, which is why the pigments thus produced are only available in small amounts.

EP-A-571 836 describes metal oxide- and metal-coated metallic interference pigments produced by gas phase coating.

Finally, U.S. Pat. No. 2,885,366 discloses the coating of aluminum platelets with silicon oxide from water glass solutions. However, the oxide layer is only applied to passivate the aluminum surface.

It is an object of the present invention to provide particularly strong metallic effect pigments producible in an economical manner.

We have found that this object is achieved by the above-defined luster pigments and their mixtures with multiply coated silicatic platelets.

As a particularly preferred variant we have found luster pigments based on multiply coated plateletlike substrates consisting essentially of aluminum comprising A) a first layer from 50 to 600 nm in thickness consisting essentially of silicon oxide, B) a second layer from 1 to 25 nm in thickness consisting essentially of molybdenum, chromium, tungsten and/or iron, and C) if desired, a third layer from 5 to 250 nm in thickness consisting essentially of silicon oxide, silicon oxide hydrate, aluminum oxide and/or aluminum oxide hydrate.

The present invention also provides a process for producing the luster pigments by subjecting the metallic substrate particles to a) wet-chemical coating with silicon oxide, aluminum oxide and/or aluminum oxide hydrate by hydrolytic decomposition of organic silicon and/or aluminum compounds in which the organic radicals are attached to the metals via oxygen atoms in the presence of an organic solvent in which the metal compounds are soluble with or without subsequent drying, and then to b1) gas phase decomposition of volatile metal compounds in an inert atmosphere or b2) electroless, wet-chemical metal deposition with or without subsequent drying, to apply a metal, or to b3) gas phase decomposition of volatile metal compounds in the presence of oxygen and/or water vapor to apply a nonselectively absorbing metal oxide and, if desired, additionally to c1) gas phase decomposition of volatile metal compounds in the presence of oxygen and/or water vapor or to c2) hydrolytic decomposition of organic metal compounds in which the organic radicals are attached to the metals via oxygen atoms in the presence of an organic solvent in which the metal compounds are soluble and subsequent drying, to apply a colorless or selectively absorbing metal oxide.

Finally, the invention also provides a process for producing the luster pigment mixtures by coating the metallic substrate particles already coated with a layer (A) and the silicatic platelets already coated with a layer (A') conjointly by step (b1), (b2) or (b3) and also optionally (c1) or (c2) with the desired layers.

The invention also provides a process for producing plateletlike metallic substrates coated with silicon oxide and/or silicon oxide hydrate, which comprises hydrolyzing organic silicon compounds in which the organic radicals are attached to the silicon via oxygen atoms in the presence of an organic solvent in which these compounds are soluble under acid or alkaline conditions and subsequently drying the substrate particles thus coated with silicon oxide and silicon oxide hydrates.

Last but not least, the invention provides for the use of these luster pigments and luster pigment mixtures for coloring coatings, inks, including printing inks, plastics, glasses, ceramic products and decorative cosmetic preparations.

Suitable substrates for the pigments of the invention are all metals and alloys in platelet form known for metallic effect pigments. Examples besides steel, copper and its alloys such as brass and bronzes are in particular aluminum and its alloys such as aluminum bronze.

Preference is given to aluminum flakes which are producible in a simple manner by stamping out of aluminum foil or by widely used atomization and grinding techniques.

Suitable aluminum pigments are produced for example by the Hall process by wet grinding in white spirits. The starting material is an atomized, irregular aluminum grit which is ball-milled in white spirits and in the presence of a lubricant into plateletlike particles and subsequently classified.

Commercial products can be used. However, the surface of the aluminum particles should be substantially free of fats or other coating media. These substances can to some extent be removed by solvent treatment or better, as described in DE-A-42 23 384, by oxidative treatment.

Furthermore, the metallic substrate particles may have been given a passivating treatment, ie. may have been given a coating which confers resistance in particular against water. Reference may be made here by way of example to Farbe+Lack 97, 4/1991, 311–314, and the references cited therein and to earlier German Patent Application P 42 36 332.2.

As used herein, the term "passivating coatings" also comprehends metal oxide layers. Examples of further suitable substrates are therefore iron oxide-coated metal pigments (eg. EP-A-33 457) with a golden to red self-color and delicately pastel-colored titanium dioxide-coated metal pigments (eg. EP-A-338 428).

The size of the substrate particles is not critical per se and can be adapted to the particular use. Generally the particles have average largest diameters from about 1 to 200 µm, in particular from about 5 to 100 µm, and thicknesses from about 0.1 to 5 µm, in particular around about 0.5 µm. Their specific free surface area (BET) is generally within the range from 0.1 to 5 $m^2/g$.

The luster pigments of the invention are notable for the metallic substrate having been coated with multiple layers.

The first layer (A) is composed of aluminum oxide, aluminum oxide hydrate and preferably silicon oxide and also of mixtures thereof.

The thickness of the layer (A) is generally from 1 to 800 nm, preferably from 50 to 600 nm. Since it is the layer (A) which essentially determines the hue of the pigments according to the invention, it has in luster pigments of the invention which exhibit a particularly pronounced color play, and are therefore preferred, a minimum thickness of about 70 nm.

As the layer thickness of (A) increases, the pigments coated with the layer (A) and the black layer (B) repeatedly pass in succession through the interference colors blue, green, gold and red under a viewing angle of 25°. The angle dependence of the hue increases from the first series of interference colors to higher series (ie. thicker layers (A)). For instance, a reddish gold of the first series will flop, depending on the angle, into a greenish gold, while such a hue in the second or third interference series flops into the complementary color, a greenish blue.

The second, nonselectively absorbing layer (B) consists essentially of metals, preferably those which can be applied by gas phase decomposition of volatile compounds, such as, in particular, molybdenum, tungsten, chromium, also cobalt and nickel or mixtures thereof, or black metal oxides, such as, in particular, magnetite, also nickel oxide, cobalt oxide (CoO, $Co_3O_4$) and vanadium oxide ($VO_2$, $V_2O_3$) and also mixtures thereof, for example iron and magnetite.

Also suitable for use in layer (B) are those metals which are wet-chemically depositable from metal salt solutions by reduction. Suitable examples are silver, copper, gold, palladium and platinum and also cobalt and nickel and alloys such as NiP, NiB, NiCo, NiWP, CoP and AgAu.

The black layer (B) must not of course be opaque, but must be partially transparent to light. In this way it reduces the white content of the incident and refracted light and thus brings about an enhancement of the barely visible interference color of the metal oxide-coated substrate.

Depending on the optical properties of the layer material (B), the layer thickness ranges generally from 1 to 100 nm. In the case of strongly absorbing, highly refractive materials such as molybdenum or chromium, a layer thickness from 1 to 25 nm is generally sufficient to achieve the desired effect. Less strongly absorbing or less refractive materials such as magnetite require thicker layers from about 10 to 50 nm.

Furthermore, the luster pigments of the invention may additionally have a third layer (C) which is composed of colorless or selectively absorbing metal oxides. Preference is given for example to aluminum oxide, aluminum oxide hydrate, zirconium oxide, titanium oxide, tin oxide, iron oxide and chromium oxide and particular preference is given to silicon oxide and silicon oxide hydrate. This top layer has the effect, in particular in the case of metallic layers (B), of distinctly improving the resistance to environmental factors.

The thickness of layer (C) is not critical per se, generally it will range from about 1 to 400 nm, especially from 5 to 250 nm.

Of course, layer (C) may likewise contribute to the interference of the pigment, continuing the interference series at the location determined by the substrate coated with (A) and (B). This is the case for example when zirconium oxide or titanium oxide is applied as layer (C). If, by contrast, layer (C) consists essentially of silicon oxide, this layer will be coloristically barely noticeable in the application medium (eg. coatings or inks) which has a similar refractive index.

Colored metal oxides such as iron oxide and chromium oxide will finally modify the interference color of the multi-layer system through admixture of their absorption color and will with increasing layer thickness finally hide it.

An embodiment of the luster pigments according to the invention which is particularly preferred on account of its high color strength comprises aluminum platelets coated with (A) silicon dioxide, (B) molybdenum, chromium, tungsten and/or iron and if desired again silicon oxide, silicon oxide hydrate, aluminum oxide and/or aluminum oxide hydrate (C), the thicknesses of the individual layers being preferably from 50 to 600 nm (A), from 1 to 25 nm, especially from 1 to 20 nm (B), and from 5 to 250 nm (C).

Altogether, in the luster pigments of the invention, all the layers have a uniform, homogeneous and filmlike structure and are capable of interference even at relatively great layer thicknesses, resulting in multi-layer systems showing strong interference colors.

For coloristic reasons, mixtures of the metallic pigments (I) according to the invention with similarly multiply coated silicatic platelets (II) are of particular interest.

Suitable silicatic substrates are in particular light-colored or white micas, flakes of preferably wet-ground muscovite being particularly preferred. It is of course also possible to use other natural micas such as phlogopite and biotite, artificial micas, talc and glass flakes.

The silicatic substrate particles used have a metal oxide layer (A') which is preferably composed of highly refractive metal oxides such as titanium oxide, zirconium oxide, zinc oxide, tin oxide, chromium oxide, iron oxide and/or bismuth oxychloride. Aluminum oxide and silicon oxide can likewise be present.

Particular preference is given to mica pigments comprising a layer (A') consisting essentially of titanium dioxide and containing the other oxides mentioned only in a minor amount, if at all.

Metal oxide-coated silicatic pigments are well-known and also commercially available under the tradenames Iriodin® (Merck, Darmstadt), Flonac® (Kemira Oy, Pori) or Mearlin® (Mearl Corporation, New York).

Suitable choice of the silicatic pigments (II) makes it possible to vary or augment the color play of the metal pigments (I).

If, for example, a metallic substrate coated with (A) and (B) shows a golden hue at a viewing angle of 25°, it can be shifted in the direction of a more reddish hue by admixing a titanium dioxide-coated mica pigment having a reddish golden interference color to the metal pigment coated only with (A) and subsequent conjoint coating with (B).

The composition of the luster pigment mixtures of the invention is not critical and is determined by the color properties desired.

In principle, the weight ratio of metallic pigment (I):silicatic pigment (II) can be varied within the range from 1:99 to 99:1. To obtain adequate hiding power, the pigment mixtures of the invention preferably contain at least 5% by weight of metallic luster pigment (I).

The preferred way of preparing the pigment mixtures of the invention is the conjoint coating of the substrate particles already coated by step (a) with layer (A) and with a layer (A'), with the black layer (B) and if desired the top layer (C).

However, it is of course also possible to apply all layers separately and to mix the coated pigments subsequently. In this case, the layers (B) and (B') and also (C) and (C') can be additionally varied.

In the process for producing the multiply coated luster pigments according to the invention, the layer (A) is applied wet-chemically by hydrolysis of organic silicon and/or aluminum compounds in which the organic radicals are attached to the metals via oxygen atoms in the presence of an organic solvent.

Suitable organic solvents for this purpose include not only aprotic solvents such as ketones, β-diketones, ethers, especially cyclic ethers, and nitrogen-containing solvents, including for example amidic solvents, but also protic solvents such as monohydric or polyhydric alcohols having preferably from 1 to 6 carbon atoms which are miscible with water.

Examples of preferred solvents are acetone, tetrahydrofuran, ethanol, n-propanol, isopropanol and also diethyl ketone, acetylacetone, dioxane, trioxane, ethylene glycol, propylene glycol, glycerol, dimethylformamide, dimethylacetamide, N-methylpyrrolidone, pyridine and acetonitrile.

Suitable metallic starting compounds are organic compounds which are soluble in the organic solvents mentioned and in which the organic radicals are attached to the metals via oxygen atoms. Preferred examples are the acetylacetonates and in particular alkoxides, especially $C_1$–$C_4$-alkoxides, eg. aluminum triisopropoxide and tetraethoxysilane.

The hydrolysis is preferably carried out in the presence of a base or acid as catalyst. Suitable for this purpose are for example, in addition to alkali metal hydroxide solutions such as sodium hydroxide solution, in particular aqueous ammonia solutions. Suitable acidic catalysts are for example phosphoric acid and organic acids such as acetic acid and oxalic acid.

Water has to be present at least in the amount required stoichiometrically for the hydrolysis, but it is preferably present in from 2 to 100 times, especially from 5 to 20 times, the amount.

Based on the amount of water used, the rule is to add from 3 to 40% by volume, preferably from 5 to 30% by volume, of a 25% strength by weight aqueous ammonia solution.

As regards the temperature management, it is advantageous to heat the reaction mixture to the reflux temperature step by step over a period from 10 to 48 h. If isopropanol is used as solvent, the mixture is preferably stirred for example initially at 40° C. for from 4 to 20 h, then at 60° C. for from 4 to 20 h and finally at 80° C. for from 2 to 8 h.

Technically, step a) of the production process according to the invention is advantageously carried out as follows:

Substrate particles, organic solvent, water and catalyst (base or acid) are charged initially and the metal compound to be hydrolyzed is added pure or dissolved, for example in the form of a from 30 to 70, preferably from 40 to 60% , strength by volume solution in the organic solvent. If the metal compound is added in one step, the suspension is subsequently heated as described above with stirring. However, the metal compound can also be metered in continuously at elevated temperature, in which case the water is preferably not included in the initial charge but likewise metered in continuously. On completion of the coating the reaction mixture is cooled back down to room temperature.

To prevent agglomeration during the coating operation, the suspension can be subjected to a strong mechanical stress such as pumping, vigorous stirring or the action of ultrasound.

If desired, the coating step can be repeated one or more times. If the mother liquor has a milky appearance, it is advisable to replace it before a further coating operation is carried out.

The substrate particles coated with the layer (A) can be isolated in a simple manner by filtration, washing with organic solvent, preferably with the alcohols used as solvent, and subsequent drying (customarily at from 20° to 200° C. for from 2 to 24 h).

The process of the invention is a trouble-free way of applying even relatively thick silicon oxide layers, of for example ≧70 nm, in good quality, ie. in the form of an unbroken, interference-capable film.

Depending on the size of the substrate particles used, it is customary to use from 10 to 60% by weight of metal oxide (A), based on the substrate to be coated, to achieve the desired color effects. For instance, relatively coarse aluminum particles (about 1.5 m$^2$/g) give attractive color effects starting from about 15% by weight of silicon oxide, while finer aluminum particles (about 4.5 m$^2$/g) require about 30% by weight of silicon oxide.

The further layers (B) and (C) are preferably applied in the process of the invention to the substrate particles coated with (A) via gas phase decomposition of volatile metal compounds (chemical vapor deposition, CVD) as described in EP-A-571 836.

For this it is advantageous to use a heatable fluidized bed reactor as described for example in EP-A-33 457 or DE-A-38 13 335, in which the substrate particles coated with (A) are initially fluidized with a gas and heated to the temperature required for the decomposition of the respective metal compound, generally to 70° to 350° C. The metal compounds vaporized in an upstream vaporizer vessel using a suitable carrier gas and the gases optionally required for the process of decomposition are then introduced via separate nozzles.

Metallic layers (B) are preferably applied by step (b1) through inert decomposition of metal carbonyls, such as iron pentacarbonyl, chromium hexacarbonyl, molybdenum hexacarbonyl, tungsten hexacarbonyl, nickel tetracarbonyl and dicobalt octacarbonyl. The decomposition temperature, for example in the case of Mo(CO)$_6$, is preferably from 200° to 250° C.

Mixed metal layers (B) consisting for example essentially of molybdenum and chromium can be applied by simultaneous or successive gas phase coating. The second option is especially relevant in the case of thin layers (B), since thorough mixing of the deposited layers takes place.

If the second, black layer is to consist of lower metal oxides, such as magnetite, VO$_2$ or V$_2$O$_3$ (step (b3)), it is advantageous to decompose the metal carbonyls such as iron pentacarbonyl or oxychlorides such as vanadium oxychloride with water vapor. If this gas phase decomposition initially deposits higher metal oxides, for example V$_2$O$_5$, they have to be subsequently reduced to the desired oxide, for example with hydrogen or ammonia.

Having been applied, the layer (B), especially if it is to form the outer layer of the luster pigment, is advantageously passivated at the surface. This may be simply done by mixing a little air into the fluidizing gases during the cooling step.

To deposit the colorless or selectively absorbing metal oxide layer (C), step (c1) preferably comprises decomposing metal carbonyls, such as iron pentacarbonyl and chromium hexacarbonyl, with oxygen (or air) and metal halides, such as silicon tetrachloride, titanium tetrachloride and zirconium tetrachloride, and metal alkoxides, such as titanium tetra-n-propoxide, titanium tetraisopropoxide, zirconium tetra-n-propoxide, and zirconium tetraisopropoxide, with water vapor.

Further details of the CVD option are described in EP-A-571 836.

However, metallic layers (B) can also be applied wet-chemically by reduction from suitable metal salt solutions (step (b2)). In this way it is possible to deposit in particular more noble metals such as copper, silver, gold, cobalt, nickel, palladium and platinum. As stated in EP-A-353 544, suitable for this purpose are a number of reducing agents, especially mild organic reducing agents such as glucose and formaldehyde.

To form the metallic layers (B) it is also possible to use metal alloys such as NiP, NiB, NiCo, NiWP, CoP and AgAu, which are likewise to be applied wet-chemically, for example by reaction of a metal salt solution with hypophosphite (EP-A-313 281).

Generally, however, the metal layers applied via the gas phase will be preferred because of their higher quality (more finely crystalline, filmlike) to those applied wet-chemically, since they usually produce more brilliant and stronger luster pigments.

Finally, the metal oxide layer (C) can likewise be applied wet-chemically as described above for the layer (A) (step (c2)). This option is advisable in particular when the layer (C) is to consist essentially of silicon oxide and/or aluminum oxide.

Depending on the completeness of the drying following step (a) or (c2), these metal oxide layers may still contain small amounts of water, ie. may exist to some extent in the form of the oxide hydrates.

The process of the invention makes it possible to produce the multiply coated metallic luster pigments reproducibly in a simple manner in large amounts. The pigment particles obtained are completely enclosed and their individual coats are of high quality.

If desired, the coated luster pigments can for the purpose of deagglomeration and smoothing be subjected to an additional refining step of gentle grinding in a ball mill or comparable apparatus.

The luster pigments of the invention and their mixtures with silicatic pigments are advantageously useful for many purposes, such as the coloring of plastics, glasses, ceramic products, decorative cosmetic preparations and in particular coatings and inks, including printing inks, especially security printing inks. All customary printing processes are suitable, for example screen printing, intaglio printing, bronze printing, flexographic printing and offset printing.

EXAMPLES

Preparation and use of luster pigments according to the invention

To incorporate the pigments in a coating, in each case 0.4 g of the pigment was suspended in 3.6 g of a polyester varnish having a solids content of 21% by weight and dispersed for 2 minutes in a Red Devil. A draw bar (wet film thickness 160 µm) was then used to prepare drawdowns of the pigmented varnish on a piece of black and white cardboard.

To evaluate the bronze printing characteristics of the pigments, sheets of paper were initially offset-printed with an unpigmented adhesive varnish (bronzing varnish) containing 95% by weight of linseed oil varnish and phenol-modified rosin ester and 5% by weight of polyvinyltoluene and then immediately passed into the bronzing station where they were dusted with the pigment. Excess pigment powder was then removed with a velvet doctor.

To evaluate the screen printing characteristics, 10 g of pigment were stirred into 90 g of a commercial binder solution (22.5 g of PVC copolymer Laroflex® MP45, 4.5 g of methoxypropyl acetate, 13.5 g of n-hexyldiglycol, 49.5 g of butylglycol). The screen printing ink thus prepared was applied with a commercial screen printing machine (screen mesh width 112–150 µm) in a thickness of 45 µm to coated, $TiO_2$-coated paper and air-dried.

EXAMPLE 1 a) In a round-bottom flask equipped with a reflux condenser and a stirrer, 150 g of aluminum powder (BET surface area 1.5 m$^2$/g) were slurried up in 750 ml of isopropanol. Following addition of a solution of 1125 ml of isopropanol, 103.3 g of water and 28.3 g of a 25% strength by weight aqueous ammonia solution, the suspension was heated to 40° C. with stirring. Following the addition of 136.3 g of tetraethoxysilane the reaction mixture was then stirred for 4 h at 40° C., for 1 h at 60° C. and for 1 h at 80° C.

After the suspension had been cooled down, the product, which still had a silvery luster, was filtered off from the mother liquor, washed with isopropanol and dried.

The coated aluminum powder had an $SiO_2$ content of 13.5% by weight and an unchanged appearance.

b) The coated aluminum powder was then heated in a fluidized bed reactor (described in EP-A-571 836) to 220° C. under fluidization with a total of 700 l/h of nitrogen. A nitrogen stream of 400 l/h was passed through an upstream vessel at 70° C. to carry over 8 h 61 g of molybdenum hexacarbonyl into the reactor, where they were decomposed into molybdenum and carbon monoxide.

On completion of the deposition of molybdenum, the fluidizing gases were admixed with a little air to passivate the molybdenum surface.

The pigment obtained had a molybdenum content of 5% by weight and, applied in the varnish, showed not only a virtually unchanged strong metallic luster but also a strong greenish blue interference color which, at relatively steep viewing angles, flopped into a reddish blue. Scanning electron micrographs showed evidence of a filmlike deposition of the molybdenum.

EXAMPLE 2 a) The aluminum powder was coated twice with $SiO_2$ by the method of Example 1a). The coated aluminum had an $SiO_2$ content of 18.8% by weight and showed a weakly golden shimmer.

b) Example 1b) was then repeated using a total of 800 l/h of nitrogen as fluidizing gas at 200° C. over 3.5 h and 18.5 g of Mo(CO)$_6$ to apply a filmlike coating of molybdenum to the coated aluminum powder.

The pigment obtained had a molybdenum content of 2.2% by weight and, applied in the varnish, showed not only a virtually unchanged strong metallic luster but also a strong reddish golden interference color which, at relatively steep viewing angles, flopped into greenish gold.

EXAMPLE 3 a) The aluminum powder was coated three times with $SiO_2$ by the method of Example 1a). The coated aluminum had an $SiO_2$ content of 29.9% by weight and showed a weakly reddish shimmer.

b) Example 1b) was then repeated using 30 g of Mo(CO)$_6$ over 6 h to apply a filmlike coating of molybdenum to the coated aluminum powder.

The pigment obtained had a molybdenum content of 3.0% by weight and, applied in the varnish, showed a strong red interference color which, at relatively steep viewing angles, flopped via gold toward green.

EXAMPLE 4 a) The aluminum powder was coated with $SiO_2$ three times by the method of Example 1a) with the difference that 150.0 g of tetraethoxysilane were used in the 3rd coating cycle. The coated aluminum had an $SiO_2$ content of 31.0% by weight and showed a weakly reddish shimmer.

b) Example 1b) was then repeated using 33 g of Mo(CO)$_6$ over 8 h to apply a filmlike coating of molybdenum to the coated aluminum powder.

The pigment obtained had a molybdenum content of 3.8% by weight and a deep purple color and, applied by screen printing, showed, at relatively steep viewing angles, a color flop toward greenish gold.

EXAMPLE 5 a) A suspension of 150 g of the aluminum powder of Example 1 in 1500 ml of isopropanol was—following addition of a solution of 500 ml of isopropanol, 100 ml of water and 30 g of a 25% strength by weight aqueous ammonia solution—heated to 40° C. with stirring. This was followed by the addition initially over 1.5 h of 136 g of tetraethoxysilane and then over 4.5 h continuously of a further 408 g of tetraethoxysilane and also at the same time a further 75 ml of water. The mixture was then stirred at 60° C. for 12 h and 80° C. for 3 h.

The coated aluminum powder isolated by the method of Example 1a) had an $SiO_2$ content of 20.8% by weight and showed a very weakly golden shimmer.

b) Example 1b) was then repeated using 25.5 g of Mo(CO)$_6$ over 5 h to apply a filmlike coating of molybdenum to the coated aluminum powder.

The pigment obtained had a molybdenum content of 1.3% by weight and a deep reddish gold color and, applied by bronze printing, showed, at relatively steep viewing angles, a color flop toward greenish gold.

EXAMPLE 6

To a suspension, protected from light, in 150 ml of water of 10 g of aluminum powder $SiO_2$-coated as in Example 5 were added 1.8 g of silver nitrate, dissolved in 40 ml of water and 3.6 ml of a 25% strength by weight aqueous ammonia solution, and 20 ml of a 75% strength by weight sodium hydroxide solution. Then a solution of 2.4 g of glucose in 150 ml of water was added dropwise over 5 h.

After stirring at room temperature for one hour, the silver-coated aluminum powder was filtered off, washed with water and dried at 60° C.

The pigment obtained had a silver content of 9.1% by weight and a weakly red color and, applied in the varnish, showed, at relatively steep viewing angles, a color flop toward greenish gold.

EXAMPLE 7 a) A slurry of 150 g of the aluminum powder of Example 1 in 750 ml of isopropanol was—following addition of a solution of 750 ml of isopropanol, 100 ml of water and 28.3 g of a 25% strength by weight aqueous ammonia solution—heated to 40° C. with stirring. This was followed by the addition initially over 2 h of 136 g of tetraethoxysilane, dissolved in 125 ml of isopropanol, and then over 5 h of a further 272 g of tetraethoxysilane, dissolved in 250 ml of isopropanol, and also at the same time a further 48 ml of water. The mixture was then stirred at 40° C. for 12 h, continuously heated over 6 h to 80° C. and stirred at that temperature for 3 h.

The coated aluminum powder isolated by the method of Example 1a) had an $SiO_2$ content of 25.7% by weight and showed a very weakly greenish shimmer.

b) The coated aluminum powder was then heated in the fluidized bed reactor to 200° C. under fluidization with a total of 800 l/h of nitrogen. A nitrogen stream of 400 l/h was passed through an upstream vessel at 20° C. to carry over 4 h 26.1 g of iron pentacarbonyl into the reactor, where they were decomposed into iron and carbon monoxide.

On completion of the deposition of iron, the fluidizing gases were admixed with a little air to passivate the iron surface.

The pigment obtained had an iron content of 3.0% by weight and a greenish golden color and, applied in the varnish, showed, at relatively steep viewing angles, a color flop toward blue.

EXAMPLE 8 a) The aluminum powder was coated twice with $SiO_2$ by the method of Example 1a) with the difference that 150.0 g of tetraethoxysilane were used in the 2nd coating cycle. The coated aluminum had an $SiO_2$ content of 24.3% by weight and showed a weakly violet shimmer.

b) The coated aluminum powder was then initially coated with chromium by the method of Example 1a) using 30 g of chromium hexacarbonyl (vaporizer temperature 80° C.) over 8 h at 240° C., the result being a more strongly violet pigment having a chromium content of 1.7% by weight.

The pigment was then additionally coated with molybdenum using 19.4 g of molybdenum hexacarbonyl (vaporizer temperature 70° C.) over 4 h at 210° C.

The pigment obtained had a molybdenum content of 1.1% by weight and, applied in the varnish, showed a strong blue interference color which, at relatively steep viewing angles, flopped toward violet.

EXAMPLE 9 a) 150 g of finely divided aluminum powder (BET surface area 4.5 $m^2/g$) was coated six times with $SiO_2$ by the method of Example 1a). The coated aluminum had an $SiO_2$ content of 45.0% by weight and showed a very weakly golden shimmer.

b) Example 1b) was then repeated using a total of 1300 l/h of nitrogen as fluidizing gas to coat the coated aluminum powder with molybdenum over 8 h using 40.0 g of $Mo(CO)_6$.

The pigment obtained had a molybdenum content of 6.1% by weight and, applied in the varnish, showed not only a strong metallic luster but also a strong reddish golden interference color which, at relatively steep viewing angles, flopped into greenish gold.

EXAMPLE 10 a) A slurry of 200 g of the aluminum powder of Example 1 in 1500 ml of isopropanol was—following addition of a solution of 500 ml of water and 40 ml of 25% strength by weight aqueous ammonia solution—heated to 60° C. with stirring. Concurrently the addition was commenced of a mixture of 600 ml of isopropanol and 600 g of tetraethoxysilane at a rate of 100 ml/h. After 12 h the entire amount had been added. After a further 12 hours of stirring, the batch was worked up by the method of Example 1.

The coated aluminum powder had an $SiO_2$ content of 24.6% by weight and showed a weakly reddish shimmer.

b) 200 g of the coated aluminum powder were then heated in the fluidized bed reactor to 300° C. under fluidization with a total of 1200 l/h of nitrogen. A proportion of the fluidizing gas (400 l/h) was passed through an upstream vessel at 80° C. to carry 48.7 g of chromium hexacarbonyl over 14 h into the reactor where they were decomposed into chromium and carbon monoxide.

On completion of the deposition of chromium, fluidizing gases were mixed with a little air to passivate the chromium surface.

The pigment obtained had a chromium content of 3.9% by weight and, applied in the varnish, showed not only a strong metallic luster but also a reddish golden interference color which, at relatively steep viewing angles, flopped toward green.

EXAMPLE 11 a) A slurry of 100 g of the aluminum powder of Example 9 in 3000 ml of isopropanol was—following addition of a solution of 1000 ml of water and 80 ml of 25% strength by weight aqueous ammonia solution—heated to 60° C. with stirring and concurrently the metered addition was commenced of a mixture of 1100 ml of isopropanol and 1100 g of tetraethoxysilane (rate of addition 100 ml/h). After 22 h the total amount had been added. After a further 20 hours of stirring, the batch was worked up by the method of Example 1.

The coated aluminum powder had an $SiO_2$ content of 73.6% by weight and showed a weak green/red flop.

b) 140 g of the coated aluminum powder were then heated in the fluidized bed reactor to 220° C. under fluidization with a total of 1000 l/h of nitrogen. A proportion of the fluidizing gas (400 l/h) was passed as per Example 10b) at 70° C. through an upstream vessel to carry 18.0 g of chromium hexacarbonyl into the reactor over 6 h.

The pigment obtained had a chromium content of 2.5% by weight and, applied in the varnish, showed not only a strong metallic luster but also a green interference color which, at relatively steep viewing angles, flopped toward red.

EXAMPLE 12 a) Example 11a) was repeated to coat the aluminum powder with $SiO_2$.

b) Example 11b) was then repeated to coat 140 g of the coated aluminum powder using 20.0 g of tungsten hexacarbonyl (temperature of upstream vessel: 80° C.) over 8 h.

The pigment obtained had a tungsten content of 5.5% by weight and, applied in the varnish, showed not only a strong metallic luster but also a green interference color which, at relatively steep viewing angles, flopped toward red.

We claim:

1. Luster pigments based on multiply coated platelet-shaped metallic substrates comprising
   A) a first layer consisting essentially of silicon oxide, silicon oxide hydrate, aluminum oxide and/or aluminum oxide hydrate, B) a second layer consisting essentially of metal and/or nonselectively absorbing metal oxide, and C) if desired, a third layer consisting essentially of colorless or selectively absorbing metal oxide, obtainable by a) wet-chemical coating of the substrate particles with silicon oxide, silicon oxide hydrate, aluminum oxide and/or aluminum oxide hydrate by hydrolytic decomposition of organic silicon and/or aluminum compounds in which the organic radicals are attached to the metals via oxygen atoms in the presence of an organic solvent in which the metal compounds are soluble with or without subsequent drying, b) further coating of the particles obtained in step a) with metal by
b1) gas phase decomposition of volatile metal compounds in an inert atmosphere or
b2) electroless, wet-chemical metal deposition with or without subsequent drying
or with nonselectively absorbing metal oxide by
b3) gas phase decomposition of volatile metal compounds in the presence of oxygen and/or water vapor and c) if desired additional coating of the particles obtained in step b) with colorless or selectively absorbing metal oxide by
c1) gas phase decomposition of volatile metal compounds in the presence of oxygen and/or water vapor or
c2) wet-chemical coating by hydrolytic decomposition of organic metal compounds in which the organic radicals are attached to the metals via oxygen atoms in the presence of an organic solvent in which the metal compounds are soluble and subsequent drying.

2. Luster pigments as claimed in claim 1 wherein the layer (B) consists essentially of chromium, molybdenum, tungsten, iron, cobalt, nickel, silver, copper, gold, palladium, platinum, nickel alloys, cobalt alloys, silver-gold alloys, magnetite, nickel oxide, cobalt oxide and/or vanadium oxide.

3. Luster pigments as claimed in claim 1 wherein the layer (C) consists essentially of silicon oxide, silicon oxide hydrate, aluminum oxide, aluminum oxide hydrate, titanium oxide, zirconium oxide, chromium oxide and/or iron oxide.

4. Luster pigments according to claim 1 wherein the metallic substrate consists essentially of passivated or nonpassivated aluminum platelets.

5. Luster pigments based on multiply coated platelet-shaped substrates consisting essentially of aluminum comprising A) a first layer from 50 to 600 nm in thickness consisting essentially of silicon oxide, B) a second layer from 1 to 25 nm in thickness consisting essentially of molybdenum, chromium, tungsten and/or iron, and C) if desired, a third layer from 5 to 250 nm in thickness consisting essentially of silicon oxide, silicon oxide hydrate, aluminum oxide and/or aluminum oxide hydrate.

6. Luster pigment mixtures of

I) the luster pigments of claim 1 and

II) multiply coated silicatic platelets comprising

A') a first layer consisting essentially of colorless or selectively absorbing metal oxide, B') a second layer consisting essentially of metal and/or nonselectively absorbing metal oxide, and C') if desired, a third layer consisting essentially of colorless or selectively absorbing metal oxide, as essential components.

7. A process for preparing luster pigments based on multiply coated platelet-shaped metallic substrates comprising A) a first layer consisting essentially of silicon oxide, aluminum oxide and/or aluminum oxide hydrate, B) a second layer consisting essentially of metal and/or nonselectively absorbing metal oxide, and C) if desired, a third layer consisting essentially of colorless or selectively absorbing metal oxide, which comprises the steps of:

a) wet-chemical coating of the substrate particles with silicon oxide, aluminum oxide and/or aluminum oxide hydrate by hydrolytic decomposition of organic silicon and/or aluminum compounds in which the organic radicals are attached to the metals via oxygen atoms in the presence of an organic solvent in which the metal compounds are soluble with or without subsequent drying, b) further coating of the particles obtained in step a) with metal by
b1) gas phase decomposition of volatile metal compounds in an inert atmosphere or
b2) electroless, wet-chemical metal deposition with or without subsequent drying
or with nonselectively absorbing metal oxide by
b3) gas phase decomposition of volatile metal compounds in the presence of oxygen and/or water vapor and c) if desired additional coating of the particles obtained in step b) with colorless or selectively absorbing metal oxide by
c1) gas phase decomposition of volatile metal compounds in the presence of oxygen and/or water vapor or
c2) wet-chemical coating by hydrolytic decomposition of organic metal compounds in which the organic radicals are attached to the metals via oxygen atoms in the presence of an organic solvent in which the metal compounds are soluble and subsequent drying.

8. A process for producing mixtures of luster pigments based on multiply coated platelet-shaped metallic substrates comprising I) luster pigments of:

A) a first layer consisting essentially of silicon oxide, silicon oxide hydrate, aluminum oxide and/or aluminum oxide hydrate, B) a second layer consisting essentially of metal and/or nonselectively absorbing metal oxide, and C) if desired, a third layer consisting essentially of colorless or selectively absorbing metal oxide, and II) multiply coated silicatic substrate platelets comprising A') a first layer consisting essentially of colorless or selectively absorbing metal oxide, B') a second layer consisting essentially of metal and/or nonselectively absorbing metal oxide, and C') if desired, a third-layer consisting essentially of colorless or selectively absorbing metal oxide, as essential components, comprising the steps of:

coating the metallic platelet-shaped substrates coated with layer A and the silicatic substrate platelet coated with layer A') conjointly by b1) gas phase decomposition of volatile metal compounds in an inert atmosphere or b2) electroless, wet-chemical metal deposition with or without subsequent drying, with metal, or by b3) gas phase decomposition of volatile metal compounds in the presence of oxygen and/or water vapor, with colorless or selectively absorbing metal oxide, and if desired additionally by c1) gas phase decomposition of volatile metal compounds in the presence of oxygen and/or water vapor or by c2) hydrolytic decomposition of organic metal compounds in which the organic radicals are attached to the metals via oxygen atoms in the presence of an organic solvent in which the metal compounds are soluble and subsequent drying, with colorless or selectively absorbing metal oxide.

9. A composition comprising coloring coatings, inks, plastics, glasses, ceramic products or decorative cosmetic preparations and luster pigments as defined in claim 1.

10. A composition comprising coloring coatings, inks, plastics, glasses, ceramic products or decorative cosmetic preparations and luster pigments as defined in claim 6.

* * * * *